(12) United States Patent
Oechsle et al.

(10) Patent No.: US 6,773,551 B1
(45) Date of Patent: Aug. 10, 2004

(54) DEVICE FOR DETERMINING THE CHARACTERISTICS OF A RUNNING MATERIAL WEB

(75) Inventors: Markus Oechsle, Bartholomä (DE); Frank Wegehaupt, Böhmenkirch (DE)

(73) Assignee: Voith Paper Patent GmbH, Heidenheim (DE)

( * ) Notice: Subject to any disclaimer, the term of this patent is extended or adjusted under 35 U.S.C. 154(b) by 0 days.

(21) Appl. No.: 09/936,516

(22) PCT Filed: Mar. 14, 2000

(86) PCT No.: PCT/EP00/02250
§ 371 (c)(1),
(2), (4) Date: Dec. 5, 2001

(87) PCT Pub. No.: WO00/55422
PCT Pub. Date: Sep. 21, 2000

(30) Foreign Application Priority Data

Mar. 15, 1999 (DE) ................................. 199 11 395

(51) Int. Cl.[7] ................................................ D21F 1/06
(52) U.S. Cl. ................ 162/198; 162/263; 162/DIG. 11; 34/446; 34/454; 34/117
(58) Field of Search ................ 162/198, 263, 162/DIG. 11; 34/446, 454, 117

(56) References Cited

U.S. PATENT DOCUMENTS

| | | |
|---|---|---|
| 3,622,448 A | 11/1971 | Adams et al. |
| 3,666,621 A | 5/1972 | Adams |
| 3,731,520 A | 5/1973 | Hickman et al. |
| 3,961,425 A | 6/1976 | Swanson et al. |

(List continued on next page.)

FOREIGN PATENT DOCUMENTS

| | | |
|---|---|---|
| DE | 6900009 | 7/1969 |
| DE | 2926072 | 1/1980 |
| DE | 3234598 | 3/1984 |
| DE | 3630561 | 3/1987 |
| DE | 3539354 | 5/1987 |

(List continued on next page.)

OTHER PUBLICATIONS

Copy of U.S. application No. 09/936,526.
Goertz: "Neue Beispiele für die Effizienz von Trockenpartieuntersuchungen" DAS PAPIER, No. 12, 1995, pp. 771–775, XP000907079.
TAPPI Proceedings 1992 Engineering Conference, pp. 629–638 and 639–654.
"Pulp & Paper Canada", 98:12(1997), pp. 111–113.
Article titled "Measurement of Reference Experimental Drying Data For The Multi–Cylinder Paper Dryer", by Stenstrom et al., pp. 1179–1186.

*Primary Examiner*—Peter Chin
*Assistant Examiner*—Mark Halpern
(74) *Attorney, Agent, or Firm*—Greenblum & Bernstein, P.L.C.

(57) ABSTRACT

Method and apparatus for determining characteristics of a running material web, the apparatus including at least one measuring device. The at least one measuring device is movable and has at least two degrees of freedom of movement. Each of the at least two degrees of freedom of movement is at least one of a rotary movement and a linear movement. The at least one measuring device is adapted to detect, at a plurality of measurement locations, data relating to at least one measured parameter. The at least one measuring device detects data about at least one of the following measured parameters: measured parameters which relate to a characteristic value of air in a region of the material web; measured parameters which relate to the material web; and other measured parameters. The method includes detecting, at a plurality of measurement locations and using the at least one measuring device, data relating to at least one measured parameter.

71 Claims, 3 Drawing Sheets

U.S. PATENT DOCUMENTS

| | | |
|---|---|---|
| 4,204,337 A | 5/1980 | Roos et al. |
| 4,614,044 A | 9/1986 | Firdler et al. |
| 5,071,514 A | 12/1991 | Francis |
| 5,145,560 A | 9/1992 | Grenlulnd |
| 5,298,122 A | 3/1994 | Munch et al. |
| 5,358,606 A | 10/1994 | Makkonen |
| 5,377,428 A | 1/1995 | Clark |
| 5,540,000 A | 7/1996 | Rosenburgh et al. |
| 5,715,158 A | 2/1998 | Chen |
| 6,024,835 A | 2/2000 | Fiore et al. |
| 6,099,620 A | 8/2000 | Arno et al. |
| 6,171,642 B1 | 1/2001 | Kustermann |
| 6,254,726 B1 | 7/2001 | Steiner et al. |

OTHER PUBLICATIONS

| | | |
|---|---|---|
| DE | 3830308 | 4/1989 |
| DE | 3901378 | 8/1989 |
| DE | 19510009 | 9/1996 |
| DE | 19542448 | 5/1997 |
| DE | 19653477 | 6/1998 |
| DE | 19654345 | 6/1998 |
| DE | 19801140 | 7/1999 |
| DE | 19844927 | 4/2000 |
| GB | 1247891 | 9/1971 |
| GB | 1266221 | 3/1972 |
| WO | 96/03616 | 2/1996 |
| WO | 99/04090 | 1/1999 |

DEVICE FOR DETERMINING THE CHARACTERISTICS OF A RUNNING MATERIAL WEB

CROSS-REFERENCE TO RELATED APPLICATIONS

The present application is a National Stage Application of International Application No. PCT/EP00/02250, filed Mar. 14, 2000. Further, the present application claims priority under 35 U.S.C. §119 of German Patent Application No. 199 11 395.5 filed on Mar. 15, 1999.

BACKGROUND OF THE INVENTION

1. Field of the Invention

The invention relates to an apparatus for the determination of characteristics of a running material web and/or of a machine for its manufacture and/or refinement, in particular for use in paper making machines, preferably in the dryer sections of paper making machines, with at least one measuring device.

2. Discussion of Background Information

For the optimization of the manufacturing process of material webs, in particular of paper webs, it is desirable to know the operating state, for example of a paper making machine, and also its behavior on changes of the machine settings as well as possible. For this purpose mathematical models are also used which describe the entire paper making machine or individual sections of the paper manufacture. For the optimization of such models and also for the control or regulation of the individual devices used in the manufacturing process, for example in a dryer section of a paper making machine, measuring devices are used in order to collect data which relate to different measured parameters, for example the moisture content of a paper web or the surface temperature of dryer cylinders. These data can serve as a basis for the models which describe the manufacture and/or refinement process and be made available to control or regulating units by which the conditions at individual machine sections can be changed, for example by controlling corresponding setting members.

Stationary measuring devices are known, with which spatially fixed measurements can be carried out with respect to one measured parameter at one measurement location, as well as scanners which include a sensor movable transverse to the web running direction.

SUMMARY OF THE INVENTION

The present invention therefore provides an apparatus of the initially named kind which can be used as universally and variably as possible and which can also be used in paper making machines.

The invention thus provides that the measuring device has at least two degrees of freedom of movement respectively corresponding to a rotary movement or a linear movement for the detection of data relating to at least one measured parameter at a plurality of measurement locations.

According to one aspect of the invention, there is provided an apparatus for determining characteristics of a running material web including at least one measuring device. The at least one measuring device is movable and has at least two degrees of freedom of movement. Each of the at least two degrees of freedom of movement is at least one of a rotary movement and a linear movement. The at least one measuring device is adapted to detect, a plurality of measurement locations, data relating to at least one measured parameter. The at least one measuring device detects data about at least one of the following measured parameters: measured parameters which relate to a characteristic value of air in a region of the material web; measured parameters which relate to the material web; and other measured parameters. The at least one measuring device may be located in at least one of a machine for manufacturing the material web, a machine for refining the material web, a paper making machine, and a dryer section. The measured parameters which relate to a characteristic value of air may comprise at least one of air temperature, air moisture, air flow, air flow direction and air flow speed. The measured parameters which relate to the material web may comprise at least one of a thickness of the material web, a temperature of the material web, and a moisture content of the material web. The other measured parameters may comprise at least one of a temperature of dry air used to dry the material web, a dew point of dry air used to dry the material web, a temperature prevailing at or in a region of a surface of a dryer cylinder of a paper making machine, a permeability at a dryer sieve, a speed of air flow that is present at a surface of a dryer sieve, air humidity at an individual machine component, and air humidity at certain locations of the material web.

The at least one measuring device may be adapted to move while it measures and without interruption from data detection. The at least one measuring device may be adapted to simultaneously carry out the at least two degrees of freedom of movement. The at least one measuring device may be adapted to carry out the at least two degrees of freedom of movement one after the other timewise.

The at least one measuring device may be movable in at least a first direction and in at least a second direction. The second direction may be perpendicular to the first direction. The at least one measuring device may be movable in at least a first direction, in at least a second direction, and in at least a third direction. The second direction may be perpendicular to the first direction and the third direction may be perpendicular to the second direction.

The at least one measuring device may be movable, with respect to a running direction of the material web, at least one of parallel to the running direction and perpendicular to the running direction. The at least one measuring device may be movable, with respect to a running direction of the material web, at least one of along the running device, transverse to the running direction, and vertically to the running direction. The at least one measuring device may be movable via a plurality of linear movements. The plurality of linear movements may comprise at least two linear movements. One of the at least two linear movements may be perpendicular to another of the at least two linear movements. The at least two linear movements may comprise three linear movements. One of the three linear movements may be perpendicular to at least one of the other two of the three linear movements.

The at least one measuring device may be rotatable about at least one axis. The at least one axis may comprise at least a first axis and at least a second axis. The second axis may be perpendicular to the first axis. The at least one axis may comprise a first axis, a second axis, and a third axis. The second axis may be perpendicular to the first axis. The third axis may be perpendicular to the second axis. The at least one measuring device may be adapted to be oriented in any desired manner in space by executing a plurality of rotary movements. The plurality of rotary movements may comprise at least two rotary movements. One of the at least two rotary movements may have a first axis and another of the at least two rotary movements may have a second axis which is perpendicular to the first axis. The at least two rotary movements may comprise three rotary movements. One of the three rotary movements may have a first axis, another of the three rotary movements may have a second axis, and still another of the three rotary movements may have a third axis, with the second axis being perpendicular to the first axis. One of the three rotary movements may have a first axis, another of the three rotary movements may have a second axis, and still another of the three rotary movements may have a third axis, with the second axis being perpendicular to the first axis and with the third axis being perpendicular to the second axis.

The at least one measuring device may be adapted to move along any desired presettable curve in space and may be adapted to be oriented in any desired manner in space be executing a plurality of linear movements and rotary movements. The plurality of linear movements and rotary movements may occur simultaneously. The plurality of linear movements and rotary movements may occur one after another timewise. At least one linear movement of the at least one measuring device may be adapted to be changeable. At least one rotational movement of the at least one measuring device may be adapted to be changeable. An orientation of the at least one measuring device may be adapted to be changeable.

The apparatus may further comprise one of a beam and a stationary frame, wherein the at least one measuring device is movable relative to the stationary frame or the beam. The at least one measuring device may be one of connected to and movably attached to at least one of a frame, a beam, and a machine. The at least one measuring device may be movably attached to a machine. The apparatus may comprise a mobile unit which can be used at different locations of a machine. The at least one measuring device may be movably connected to a joint. The joint may comprise at least one of a ball joint and a joint which enables a pivotal movement in at least one plane. The at least one measuring device may comprise at least one exchangeable measuring head. The apparatus may be adapted to utilize a plurality of different measuring devices. The at least one measuring device may be adapted to utilize a plurality of exchangeable measuring heads. The at least one measuring device may comprise a plurality of measuring devices. The plurality of measuring devices may comprise interchangeable measuring heads. Each of the plurality of measuring devices may be adapted to measure a different parameter.

The apparatus may further comprise at least one of a common operation unit and a control unit associated with the at least one measuring device. The apparatus may further comprise at least one of a drive unit, a supply unit, a data detection unit and an evaluation unit associated with the at least one measuring device. The apparatus may further comprise a frame, wherein the at least one measuring device is coupled to a frame. The frame may extend transverse to a running direction of the material web. The frame may be located beneath the material web. The frame may be located in a region of one of a dryer cylinder and a dryer roll. The frame may be located in a paper making machine, the frame being supported on both sides of the paper making machine. The at least one measuring device may be coupled to a beam. The beam may be one of vertically oriented and transversely oriented relative to a running direction of the material web. The beam may be located in a dryer section of a paper making machine. The at least one measuring device may be movably disposed in a cellar of a dryer section of a paper making machine. The apparatus may further comprise a protective device for protecting the at least one measuring device. The protective device may be adapted to protect against downwardly falling articles. The protective device may comprise at least one of a scraper and a sheet metal shield. The apparatus may further comprise at least one of an electrical, a pneumatic, and a hydraulic drive for moving the at least one measuring device. The at least one measuring device may be adapted to be manually movable. The at least one measuring device may be rotatable about at least one axis and so as to be able to detect at least one measured parameter at a plurality of measurement locations.

The invention additionally provides for an apparatus for determining characteristics of a running material web in a paper making machine. The apparatus includes at least one measuring device. The at least one measuring device is movable and has at least two degrees of freedom of movement. At least one of the at least two degrees of freedom of movement is a rotary movement. At least another of the at least two degrees of freedom of movement is a linear movement. The at least one measuring device is adapted to detect, at a plurality of measurement locations, data relating to at least one measured parameter. The at least one measuring device detects data about at least one of a parameter relating to a characteristic value of air in a region of the material web and a parameter which relates to the material web.

The invention also provides for a method for determining characteristics of a running material web using an apparatus for determining characteristics of a running material web which includes at least one measuring device, the at least one measuring device being movable and having at least two degrees of freedom of movement, each of the at least two degrees of freedom of movement being at least one of a rotary movement and a linear movement. The method includes detecting, at a plurality of measurement locations and using the at least one measuring device, data relating to at least one measured parameter. The at least one measuring device detects data about at least one of the following measured parameters: measured parameters which relate to a characteristic value of air in a region of the material web; measured parameters which relate to the material web; and other measured parameters.

The at least one measuring device may be located in at least one of a machine for manufacturing the material web, a machine for refining the material web, a paper making machine, and a dryer section. The measured parameters which relate to a characteristic value of air may comprise at least one of air temperature, air moisture, air flow, air flow direction and air flow speed. The measured parameters which relate to the material web may comprise at least one of a thickness of the material web, a temperature of the material web, and a moisture content of the material web. The other measured parameters may comprise at least one of a temperature of dry air used to dry the material web, a dew point of dry air used to dry the material web, a temperature prevailing at or in a region of a surface of a dryer cylinder of a paper making machine, a permeability at a dryer sieve, a speed of air flow that is present at a surface of a dryer sieve, air humidity at an individual machine component, and air humidity at certain locations of the material web.

Degrees of freedom of movement or degrees of freedom are used here to describe movements of the measuring device which can each not be produced by combinations of other movements respectively corresponding to one degree of freedom. Through the invention an apparatus is provided with a measuring device which can be moved in diverse manner and which can be ideally aligned as a result of its mobility with the individual measurement locations, and in particular can be used in regions of the paper making machine to which access is difficult, for example between the dryer cylinders of a dryer section of the paper making machine. The provision of a plurality of degrees of freedom makes it possible to intentionally so align the measuring device or a sensor of the measuring device that different measurement locations can be targeted one after the other which can, for example, not be reached with a scanner which is only movable along a straight line. The material web or machine to be investigated can be scanned with the measuring device of the invention also following any desired irregular pattern by investigating measurement locations distributed irregularly over the material web, the machine and/or the environment of the material web or machine one after the other. The investigation of the environment relates in this respect for example to the detection of data concerning a measured parameter which relates to a characteristic value of the air, for example its temperature or moisture, or of an air flow, for example its direction or speed, in the region of the material web or of the machine. The provision in accordance with the invention of a plurality of degrees of freedom also makes it possible to position the measuring device in two steps by it first being moved, for example by a linear movement, into the vicinity of the respective measurement location and by it being orientated, subsequent to this coarse adjustment, as part of a fine adjustment, for example, by a rotary movement such that the respective measurement location is precisely targeted. Each measurement location can thus be moved to quickly and nevertheless with a high precision, and in particular in a reproducible manner, by an appropriate design of the drive of the measuring device.

In accordance with a preferred embodiment of the invention, the measuring device is movable during the measurement and in particular without interruption of the data detection.

In this way, profiles of the respective measured parameter having any shape can be recorded at the material web or at the machine, and indeed in particular also transverse profiles and profiles in the longitudinal direction of the material web or in the direction of the machine or the process.

In accordance with a further preferred embodiment of the invention, the measuring device is simultaneously able to carry out a plurality of movements each corresponding to one degree of freedom.

The versatility of the measuring device of the invention is further increased in this manner. The measuring device can also already be preset within the framework of a coarse adjustment during the moving towards each measurement location to be investigated such that the subsequent fine adjustment only requires very little time.

In accordance with a further preferred embodiment of the invention, the measuring device is movable along three longitudinal axes preferably extending perpendicular to one another.

In this way, each point of a Cartesian coordinate system can be moved to with the measuring device, with the measuring device, in a particularly preferred variant, being movable in the longitudinal direction of the material web, perpendicular to the direction of movement of the web and in a vertical direction.

In a further preferred variant, the measuring device can additionally be rotatable about three axes which preferably extend perpendicular to one another, with the rotational axes being able to coincide with the three longitudinal axes which extend pair-wise perpendicular to one another. In this way, a measuring device having six degrees of freedom is provided which is characterised by a particularly high movement ability and thus versatility.

The measuring device can also have degrees of freedom corresponding exclusively to each rotary movement, also without the possibility of linear movements, and be rotatably mounted, for example, about two or three rotational axes which each stand pair-wise perpendicular to one another.

In accordance with a further preferred embodiment of the invention, the orientation of at least one longitudinal axis and/or rotational axis of the measuring device can be changed in space. This can be realised, for example, in that the measuring device is attached to a beam or frame which is movable relative to the material web or the machine in order to change in this way the location of a track or of a joint for the measuring device and thus the respective longitudinal or rotational axis in space.

It is also possible to movably attach the measuring device directly to the machine without such beams or frames.

Furthermore, the measuring device can be provided in the form of a mobile unit which can be used at different positions of a machine. Such a measuring device can in particular be used for corrective measurements, for example for defect or error location.

In accordance with a further preferred embodiment of the invention, the measuring device is movable via a joint, in particular via a ball joint, which enables a pivotal movement in at least one plane.

A particularly good movability of the measuring device results in this way. A ball joint allows the carrying out of pivotal or rotational movements about a plurality of axes in simple manner. A measuring device which can be used in particularly versatile manner can be provided simply by a combination of the pivotal or rotational movements enabled by way of the joint with a single linear movement.

In accordance with a further preferred embodiment of the invention, a plurality of measuring devices, in particular provided in the form of interchangeable measuring heads, can be combined into one unit.

The measuring devices can, for example, be attached to a common frame or beam via which the individual measuring devices can be connected to a common control unit, drive unit, supply unit, data detection unit and/or evaluation unit. A particularly efficient utilisation of the individual components results in this manner. The investigation of the material web or of the machine with respect to different measured parameters can take place by the simultaneous use of measuring devices of different design or by the use of interchangeable measuring devices or measuring heads. For this purpose, the frame or the beam, to which the interchangeable measuring device or measuring heads can be attached, is preferably provided with at least one measuring location compatible with the individual measuring devices.

In accordance with a further preferred embodiment of the invention, the measuring device is attached to a frame which preferably extends transverse to the web running direction beneath the machine or over the machine and which is preferably supported on both sides of the machine.

In this manner, the measuring device can be moved, for example in the manner of a hangar crane, beneath or above the dryer section of a paper making machine in order, for example, to scan a dryer cylinder of the dryer section, with the measuring device being used as a service device for fast and simple diagnostic measurements in particular at new machines.

If, in accordance with a preferred variant, the frame is movable in the running direction of the material web or in the direction of the machine or the process, data can be collected about a plurality of dryer cylinders arranged in series. The measuring device can additionally be movable in the vertical direction and, for this purpose, be arranged for example at the free end of a beam extending in the vertical direction. The measuring device can in this way, for example, be raised or lowered into intermediate spaces between dryer cylinders spaced in the machine direction.

The invention also provides that the measuring device is rotatable about an axis at a plurality of measurement locations for the detection of data relating to at least one measured parameter.

Such a measuring device can, for example, be attached to a beam projecting in the vertical direction or transversely to the web running direction into a machine, for example into intermediate spaces between suction rolls or dryer cylinders. In this manner, a plurality of measurement locations at the material web or at the machine can be investigated without having to move the beam relative to the machine or to linearly move the measuring device relative to the beam.

Generally any kind of measuring apparatus can be used as the measuring device with which the material web, the machine or the environment can be investigated with respect to at least one parameter relevant to the manufacturing or refining process. Possibilities include, for example, sensors working with visible, for example, polarised, light, sensors generally designed for the emission and for the reception of electromagnetic radiation, for example IR sensors, sensors working with electrically charged particles, measuring devices equipped with temperature sensors, moisture sensors or devices for the investigation of air flows. The measured parameters with respect to which, for example, a paper web, the dryer cylinders and/or dryer sieves can be investigated in dryer sections of paper making machines are, for example, the thickness, the temperature or the moisture content of the material web or the paper web, the temperature and/or the dew point of the dry air used to dry the material web, the temperature prevailing at or in the region of the surface of the dryer cylinders of a paper making machine, the permeability at dryer sieves, the speed of air flows present in particular at the surface of dryer sieves or the humidity at the individual machine components or at certain locations of the material web.

Further preferred embodiments of the invention are set forth in the claims, in the description and in the drawings.

BRIEF DESCRIPTION OF THE DRAWINGS

The present invention is further described in the detailed description which follows, in reference to the noted plurality of drawings of embodiments of the present invention, in which like reference numerals represent similar parts throughout the several views of the drawings, and wherein.

DETAILED DESCRIPTION OF THE INVENTION

Figure 1:
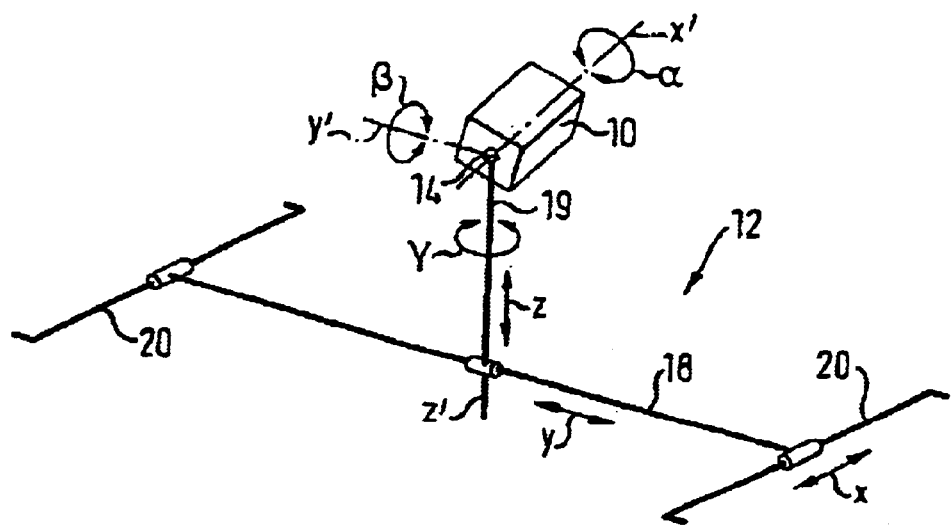
FIGS. 1 and 2 show perspective schematic illustrations in each case of a measuring apparatus in accordance with an embodiment of the invention having a plurality of degrees of freedom.

In FIG. 1, a measuring device 10 of an apparatus of the invention which is attached to a frame 12 shown schematically in FIG. 1 is indicated by a parallelpiped. The frame 12 includes a cross member 18 serving as a beam which extends over a paper making machine (not shown) and is supported at the base at both sides of the machine via support elements 20.

The measuring device 10 is attached to the free end of a vertically extending beam 19 which is coupled to the cross member 18.

The cross member 18 is movable relative to the support elements 20 in the running direction of the material web or in the direction x of the machine or process. It is also possible to provide support elements 20 movable in the x direction to which the cross member 18 is fixedly connected. The vertical beam 19 is in turn movable relative to the cross member 18 in a transverse direction y extending perpendicular to the machine direction x. The vertical beam 19 is also movable in the direction of its longitudinal extent relative to the cross member 18, so that the measuring device 10 can in this way be moved in the vertical direction z. It is also possible to provide a vertical beam 19 rigidly connected to the cross member 18 and a measuring device 10 movable relative thereto and thus in the z direction.

The arrangement explained above enables the measuring device to be moved to and fro in directions x, y, z extending in each case pair-wise perpendicular to one another and thus to be positioned at any location in space.

Furthermore, the measuring device 10 is attached to the beam 19 via a joint 14, for example a ball joint, and rotatable about three rotational axes x', y', z' each extending pair-wise perpendicular to one another, and indeed each in both directions and about at least almost 360°, as indicated by arrows α, β, γ in FIG. 1. In the embodiment shown, a rotational axes z' coincides with the vertical direction z defined by the vertical beam 19, whereas the two other rotational axes x', y' are each offset parallel to the corresponding longitudinal directions x, y.

The rotation of the measuring device 10 about the vertical axis y' or y can take place by the rotational mounting of the measuring device 10 at the vertical beam 19 or by rotation of the vertical beam 19 about its own longitudinal axis.

The measuring device 10 of FIG. 1 has six degrees of freedom with the three linear movements and the three rotational movements and can thus be moved to any point in space, on the one hand, and oriented anywhere in space at this point, on the other hand.

Figure 2:
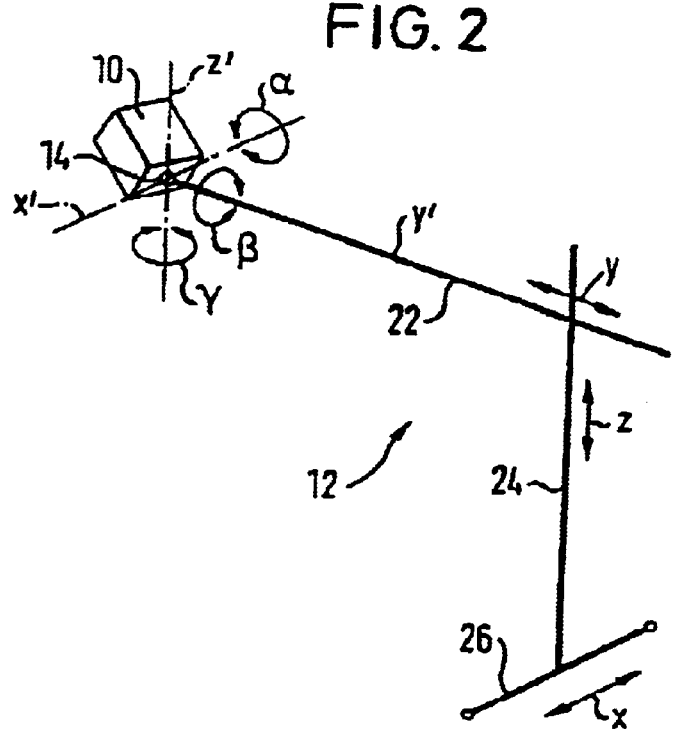

FIG. 2 shows a measuring device 10 which likewise has six degrees of movement freedom and which is movable along longitudinal axes x, y z oriented in accordance with FIG. 1 and each extending pair-wise perpendicular to one another. In contrast to the embodiment of FIG. 1, the measuring device 10 is attached to the free end of a beam or boom 22 extending in the transverse direction y via a joint 14, for example a ball joint, such that the measuring device 10 can be rotated about rotational axes x', y', z' likewise oriented in accordance with FIG. 1 and each extending pair-wise perpendicular to one another. In this embodiment, the rotational axis y' coincides with the longitudinal axis y of the boom 22 extending transversely to the web running direction or the direction x of the machine or process.

The boom 22 is coupled to a vertical beam 24 and is movable in the direction of its longitudinal extent y relative to the beam 24. It is also possible to provide a rigid connection between the boom 22 and the vertical beam 24 and to provide the measuring device 10 movably along the boom 22.

The lower end of the vertical beam 24 is connected to a support element 26 extending in the machine direction x. The movability of the measuring device 10 in the x direction can be realised by moving the support element 26 in the x direction or by moving the vertical beam 24 along the support element 26.

With the embodiment of FIG. 2, a crane-like frame 12 is provided whose free end, which bears the measuring device 10, can be moved to any point in space to which the measuring device 10 can be oriented anywhere in space by turning about the axes x', y', z' in each case by at least almost 360°.

Figure 3:
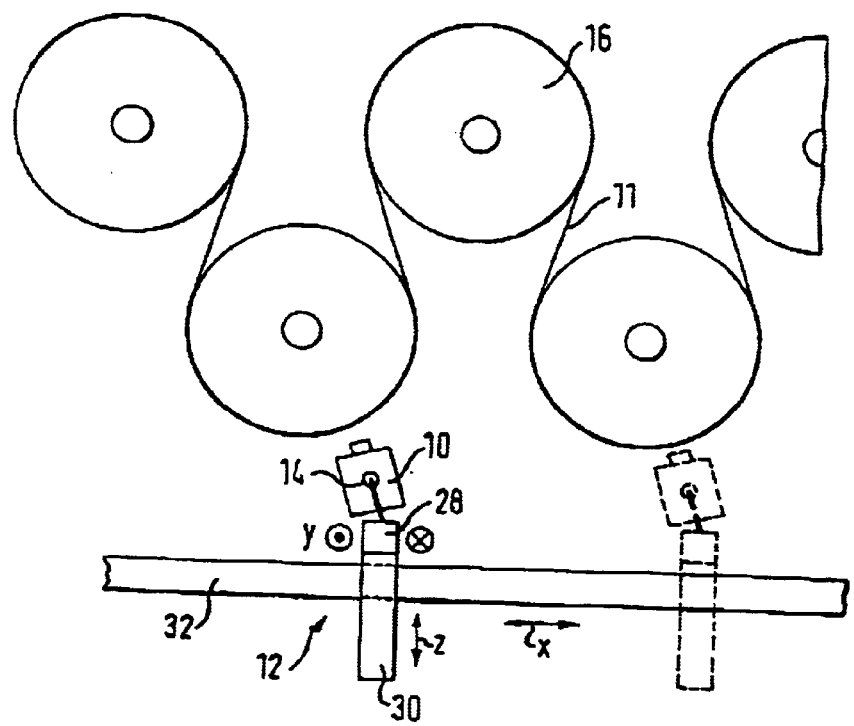
FIG. 3 shows a schematic side view of a measuring apparatus in accordance with a further embodiment of the invention used at dryer cylinders of a drying section in a paper making machine.

FIG. 3 shows the use of an apparatus of the invention which has a measuring device 10, which is attached to a frame 12 and likewise has six degrees of freedom, in a dryer section of a paper making machine, with the measuring device 10 being located beneath a row of dryer cylinders 16 which are arranged in offset manner and around which a paper web 11 to be dried is guided.

The measuring device 10 is attached to a joint 14, formed for example as a ball joint, which allows a rotation or pivoting of the measuring device 10 about rotational axes which can generally be oriented anywhere in space.

The joint 14 is connected to a cross member 28 serving as a beam which extends in the transverse direction y perpendicular to the direction x of the machine or process and is movable relative to the measuring device 10 attached to the joint 14. The cross member 28 in this manner forms a traversing track for the measuring device 10.

The cross member 28 is attached to a vertical beam 30 which extends in the vertical direction z and is movable in the vertical direction z in order to provide a vertical movement of the measuring device 10 in this manner.

The vertical beam 30 is movable along a support element 32 which extends in the machine direction x and which thus represents a track carrier enabling movements of the measuring device 10 in the machine direction x. The measuring device 10 can in this way be moved to and fro between the dryer cylinders 16 spaced in the machine direction x, as is indicated by the arrangement illustrated only in outline in the right hand part of FIG. 3.

It can be seen from FIG. 3 that, for example, by a simultaneous movement of the measuring device 10 in the machine direction x and in the vertical direction z and by a rotation of the measuring device 10 about a rotational axis extending in the transverse direction y, a dryer cylinder 16 can be scanned such that a constant spacing is observed between the cylinder surface and the side of the measuring device 10 confronting the dryer cylinder 16.

Figure 4:
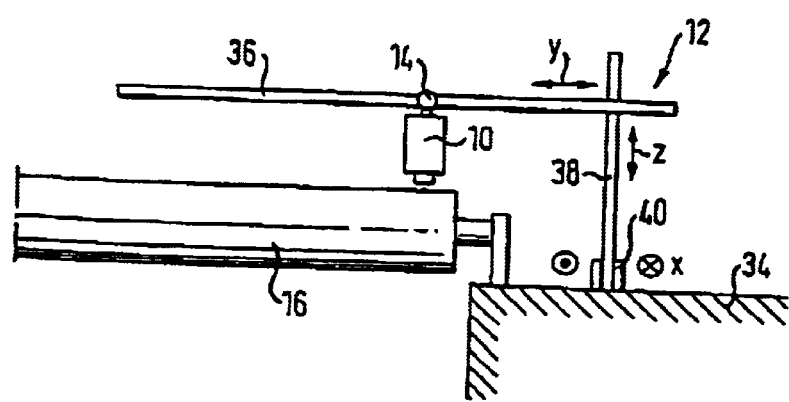
FIG. 4 shows a schematic view in the machine direction of a measuring apparatus in accordance with a further embodiment of the invention used at a dryer cylinder.

FIG. 4 shows a measuring device 10 which is attached to a frame 12 formed in accordance with FIG. 2 and which likewise has six degrees of freedom for the carrying out of measurements at a dryer cylinder 16. The frame 12 can be installed at the operator side or the drive side of the paper making machine. The measuring device 10 is attached to a joint 14, provided for example in the form of a ball joint, and is arranged suspended from a beam or boom 36 such that the free end of the measuring device 10 is located in the vicinity of the cylinder surface.

In accordance with the embodiment of FIG. 2, the boom 36 is movable relative to a vertical beam 38 which is in turn movable relative to a support element 40 fixedly connected to the base 34 also serving for the support of the dryer cylinder 16.

In accordance with the invention, the measuring device 10 can also be attached directly to the respective machine without a frame 12, as is illustrated for example in the embodiments of FIGS. 1 to 4, and be movably mounted in the manner of the invention.

Figure 5:
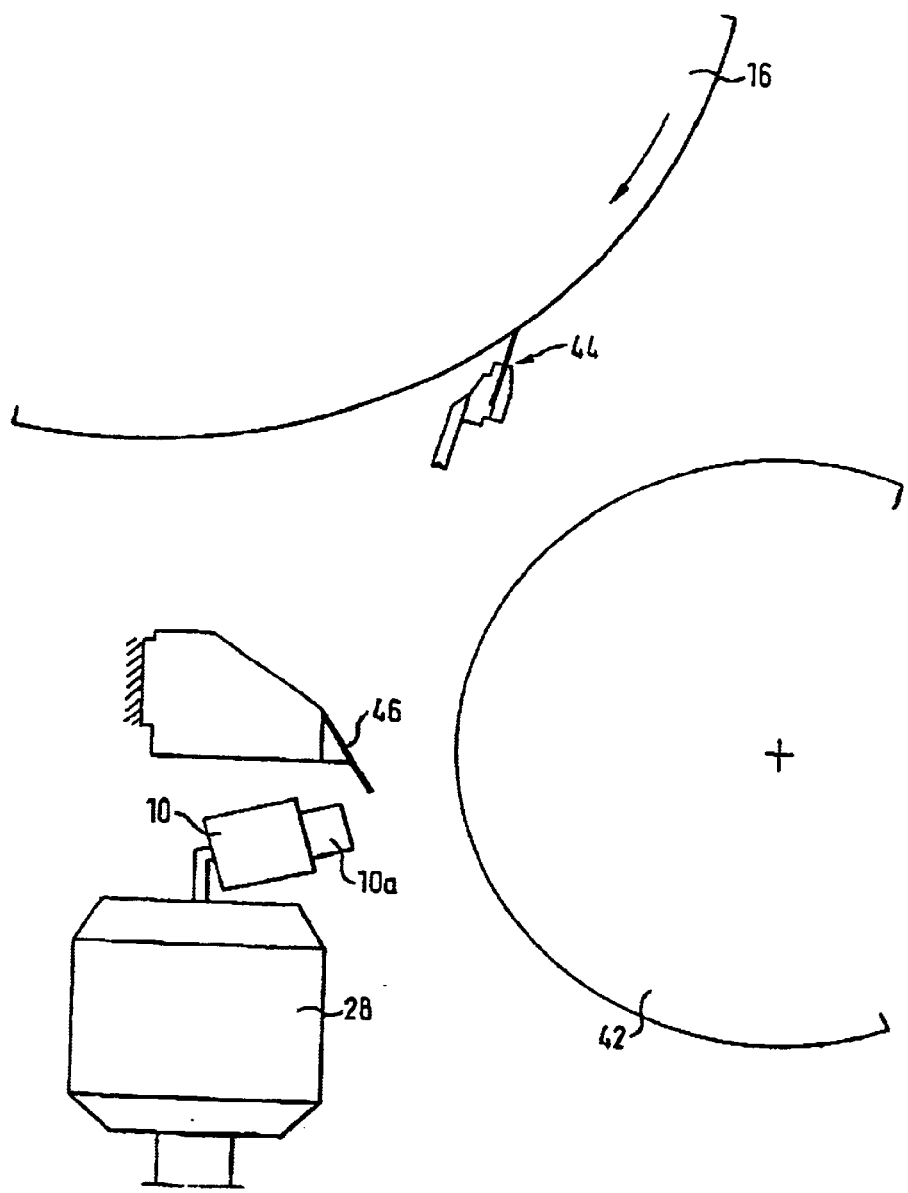
FIG. 5 shows a schematic side view of a measuring apparatus in accordance with a further embodiment of the invention used in a dryer section of a paper making machine and protected by a protective device.

In FIG. 5, the measuring device 10, which corresponds for example with respect to its travel and movement capability to a measuring device described above in connection with FIGS. 1 to 4 and which is movably attached to a cross member 28, serves for the investigation of the relationships at a suction roll 42 of a dryer section of a paper making machine.

The measuring device 10 is located beneath a dryer cylinder 16 at which a scraper 44 is arranged. A protective device formed by a sheet metal shield 46 is provided for the protection of the measuring devices 10 against paper or paper residues detached from the dryer cylinder 16 by way of the scraper 44. The measuring device 10 is protected from above by the sheet metal shield 46 without impairing the measurements carried out by way of a measuring region 10a confronting the suction roll 42. The sheet metal shield 46 can be fixedly attached to the machine and extend along the whole movement region of the measuring device 10. It is also possible to mount the sheet metal shield 46 or another protective device to the movable measuring device 10.

Furthermore, a correspondingly designed scraper 44 can alternatively or additionally serve as a protective device for the measuring device 10 and, for example, be provided with a downwardly extending metal sheet which shields the measuring device 10 from downwardly falling articles.

The measuring device 10 is also protected in the case of a web tear by a protective device of the kind described above.

What is claimed is:

1. An apparatus for determining characteristics of a running material web comprising:
    at least one measuring device;
    the at least one measuring device being movable and having at least two degrees of freedom of movement;
    each of the at least two degrees of freedom of movement being at least one of a rotary movement and a linear movement;
    the at least one measuring device being adapted to detect, at a plurality of measurement locations, data relating to at least one measured parameter; and
    the at least one measuring device detecting data about at least one of the following measured parameters:
        measured parameters which relate to a characteristic value of air in a region of the material web;
        measured parameters which relate to the material web; and other measured parameters,
    wherein the at least one measuring device moves along the at least two degrees of freedom of movement during data detection.

2. The apparatus of claim 1, wherein the at least one measuring device is located in at least one of a machine for manufacturing the material web, a machine for refining the material web, a paper making machine, and a dryer section.

3. The apparatus of claim 1, wherein the measured parameters which relate to a characteristic value of air comprise at least one of air temperature, air moisture, air flow, air flow direction and air flow speed.

4. The apparatus of claim 1, wherein the measured parameters which relate to the material web comprise at least one of a thickness of the material web, a temperature of the material web, and a moisture content of the material web.

5. The apparatus of claim 1, wherein the other measured parameters comprise at least one of a temperature of dry air used to dry the material web, a dew point of dry air used to dry the material web, a temperature prevailing at or in a region of a surface of a dryer cylinder of a paper making machine, a permeability at a dryer sieve, a speed of air flow that is present at a surface of a dryer sieve, air humidity at an individual machine component, and air humidity at certain locations of the material web.

6. The apparatus of claim 1, wherein the at least one measuring device moves while it measures without interruption from data detection.

7. The apparatus of claim 1, wherein the at least one measuring device is adapted to simultaneously carry out the at least two degrees of freedom of movement.

8. The apparatus of claim 1, wherein the at least one measuring device is adapted to carry out the at least two degrees of freedom of movement, one after the other timewise.

9. The apparatus of claim 1, wherein the at least one measuring device is movable in at least a first direction and in at least a second direction.

10. The apparatus of claim 9, wherein the second direction is perpendicular to the first direction.

11. The apparatus of claim 1, wherein the at least one measuring device is movable in at least a first direction, in at least a second direction, and in at least a third direction.

12. The apparatus of claim 11, wherein the second direction is perpendicular to the first direction and wherein the third direction is perpendicular to the second direction.

13. The apparatus of claim 1, wherein the at least one measuring device is movable, with respect to a running direction of the material web, at least one of parallel to the running direction and perpendicular to the running direction.

14. The apparatus of claim 1, wherein the at least one measuring device is movable, with respect to a running direction of the material web, at least one of along the running direction, transverse to the running direction, and vertically to the running direction.

15. The apparatus of claim 1, wherein the at least two degrees of freedom of movement comprise at least two linear movements.

16. The apparatus of claim 15, wherein one of the at least two linear movements is perpendicular to another of the at least two linear movements.

17. The apparatus of claim 15, wherein the at least two linear movements comprises three linear movements.

18. The apparatus of claim 17, wherein one of the three linear movements is perpendicular to at least one of the other two of the three linear movements.

19. The apparatus of claim 1, wherein the at least one measuring device is rotatable about at least one axis.

20. The apparatus of claim 19, wherein the at least one axis comprises at least a first axis and at least a second axis.

21. The apparatus of claim 20, wherein the second axis is perpendicular to the first axis.

22. The apparatus of claim 19, wherein the at least one axis comprises a first axis, a second axis, and a third axis.

23. The apparatus of claim 22, wherein the second axis is perpendicular to the first axis.

24. The apparatus of claim 23, wherein the third axis is perpendicular to the second axis.

25. The apparatus of claim 1, wherein the at least one measuring device is adapted to be oriented in any desired manner in space by executing a plurality of rotary movements.

26. The apparatus of claim 25, wherein the plurality of rotary movements comprise at least two rotary movements.

27. The apparatus of claim 25, wherein one of the plurality of rotary movements has a first axis and another of the plurality of rotary movements has a second axis which is perpendicular to the first axis.

28. The apparatus of claim 25, wherein the at least two rotary movements comprise three rotary movements.

29. The apparatus of claim 28, wherein one of the three rotary movements has a first axis, another of the three rotary movements has a second axis, and still another of the three rotary movements has a third axis, with the second axis being perpendicular to the first axis.

30. The apparatus of claim 28, wherein one of the three rotary movements has a first axis, another of the three rotary movements has a second axis, and still another of the three rotary movements has a third axis, with the second axis being perpendicular to the first axis and with the third axis being perpendicular to the second axis.

31. The apparatus of claim 1, wherein the at least one measuring device is adapted to move along any desired presettable curve in space and is adapted to be oriented in any desired manner in space by executing a plurality of linear movements and rotary movements.

32. The apparatus of claim 31, wherein the plurality of linear movements and rotary movements occur simultaneously.

33. The apparatus of claim 31, wherein the plurality of linear movements and rotary movements occur one after another timewise.

34. The apparatus of claim 1, wherein at least one linear movement of the at least one measuring device is adapted to be changeable.

35. The apparatus of claim 1, wherein at least one rotational movement of the at least one measuring device is adapted to be changeable.

36. The apparatus of claim 1, wherein an orientation of the at least one measuring device is adapted to be changeable.

37. The apparatus of claim 1, further comprising one of a beam and a stationary frame, wherein the at least one measuring device is movable relative to the one of a beam and a stationary frame.

38. The apparatus of claim 1, wherein the at least one measuring device is one of connected to and movably attached to at least one of a frame, a beam, and a machine.

39. The apparatus of claim 1, wherein the at least one measuring device is movably attached to the machine.

40. The apparatus of claim 1, wherein the apparatus comprises a mobile unit which can be used at different locations on a machine.

41. The apparatus of claim 1, wherein the at least one measuring device is movably connected to a joint.

42. The apparatus of claim 41, wherein the joint comprises at least one of a ball joint and a joint which enables a pivotal movement in at least one plane.

43. The apparatus of claim 1, wherein the at least one measuring device comprises at least one exchangeable measuring head.

44. The apparatus of claim 1, wherein the apparatus is adapted to utilize a plurality of different measuring devices.

45. The apparatus of claim 1, wherein the at least one measuring device is adapted to utilize a plurality of exchangeable measuring heads.

46. The apparatus of claim 1, wherein the at least one measuring device comprises a plurality of measuring devices.

47. The apparatus of claim 46, wherein the plurality of measuring devices comprises interchangeable measuring heads.

48. The apparatus of claim 46, wherein each of the plurality of measuring devices is adapted to measure a different parameter.

49. The apparatus of claim 1, further comprising at least one of a common operation unit and a control unit associated with the at least one measuring device.

50. The apparatus of claim 1, further comprising at least one of a drive unit, a supply unit, a data detection unit and an evaluation unit associated with the at least one measuring device.

51. The apparatus of claim 1, further comprising a frame, wherein the at least one measuring device is coupled to the frame.

52. The apparatus of claim 51, wherein the frame extends transverse to a running direction of the material web.

53. The apparatus of claim 52, wherein the frame is located beneath the material web.

54. The apparatus of claim 52, wherein the frame is located in a region of one of a dryer cylinder and a dryer roll.

55. The apparatus of claim 51, wherein the frame is located in a paper making machine, the frame being supported on both sides of the paper making machine.

56. The apparatus of claim 1, wherein the at least one measuring device is coupled to a beam.

57. The apparatus of claim 56, wherein the beam is one of vertically oriented and transversely oriented relative to a running direction of the material web.

58. The apparatus of claim 57, wherein the beam is located in a dryer section of a paper making machine.

59. The apparatus of claim 1, wherein the at least one measuring device is movably disposed in a cellar of a dryer section of a paper making machine.

60. The apparatus of claim 1, further comprising a protective device for protecting the at least one measuring device.

61. The apparatus of claim 60, wherein the protective device is adapted to protect against downwardly falling articles.

62. The apparatus of claim 60, wherein the protective device comprises at least one of a scraper and a sheet metal shield.

63. The apparatus of claim 1, further comprising at least one of an electrical, a pneumatic, and a hydraulic drive for moving the at least one measuring device.

64. The apparatus of claim 1, wherein the at least one measuring device is adapted to be manually movable.

65. The apparatus of claim 1, wherein the at least one measuring device is rotatable about at least one axis and so as to be able to detect at least one measured parameter at a plurality of measurement locations.

66. An apparatus for determining characteristics of a running material web in a paper making machine, the apparatus comprising:
at least one measuring device;
the at least one measuring device being movable and having at least two degrees of freedom of movement;
at least one of the at least two degrees of freedom of movement being a rotary movement;
at least another of the at least two degrees of freedom of movement being a linear movement;
the at least one measuring device being adapted to detect, at a plurality of measurement locations, data relating to at least one measured parameter; and
the at least one measuring device detecting data about at least one of a parameter relating to a characteristic value of air in a region of the material web and a parameter which relates to the material web,
wherein the at least one measuring device moves along the at least two degrees of freedom of movement during data detection.

67. A method for determining characteristics of a running material web using an apparatus for determining characteristics of a running material web which includes at least one measuring device, the at least one measuring device being movable and having at least two degrees of freedom of movement, each of the at least two degrees of freedom of movement being at least one of a rotary movement and a linear movement, the method comprising:
moving the at least one measuring device along the at least two degrees of freedom of movement; and
during the moving, detecting data relating to at least one measured parameter, at a plurality of measurement locations and using the at least one measuring device,
wherein the at least one measuring device is adapted to detect data about at least one of the following measured parameters:
measured parameters which relate to a characteristic value of air in a region of the material web;
measured parameters which relate to the material web; and
other measured parameters.

68. The method of claim 67, wherein the at least one measuring device is located in at least one of a machine for manufacturing the material web, a machine for relining the material web, a paper making machine, and a dryer section.

69. The method of claim 67, wherein the measured parameters which relate to a characteristic value of air comprise at least one of air temperature, air moisture, air flow, air flow direction and air flow speed.

70. The method of claim 67, wherein the measured parameters which relate to the material web comprise at least one of a thickness of the material web, a temperature of the material web, and a moisture content of the material web.

71. The method of claim 67, wherein the other measured parameters comprise at least one of a temperature of dry air used to dry the material web, a dew point of dry air used to dry the material web, a temperature prevailing at or in a region of a surface of a dryer cylinder of a paper making machine, a permeability at a dryer sieve, a speed of air flow that is present at a surface of a dryer sieve, air humidity at an individual machine component, and air humidity at certain locations of the material web.

* * * * *